(12) United States Patent
Patel et al.

(10) Patent No.: US 12,390,671 B2
(45) Date of Patent: *Aug. 19, 2025

(54) METHOD AND APPARATUS FOR PROVIDING AIR FLOW

(71) Applicant: Illinois Tool Works Inc., Glenview, IL (US)

(72) Inventors: Nishank R. Patel, Appleton, WI (US); Eric Sommers, Appleton, WI (US); Joseph C. Schneider, Menasha, WI (US)

(73) Assignee: Illinois Tool Works Inc., Glenview, IL (US)

( * ) Notice: Subject to any disclaimer, the term of this patent is extended or adjusted under 35 U.S.C. 154(b) by 61 days.

This patent is subject to a terminal disclaimer.

(21) Appl. No.: 18/162,271

(22) Filed: Jan. 31, 2023

(65) Prior Publication Data
US 2023/0181940 A1 Jun. 15, 2023

Related U.S. Application Data

(63) Continuation of application No. 16/721,969, filed on Dec. 20, 2019, now Pat. No. 11,596,815, which is a
(Continued)

(51) Int. Cl.
*A62B 18/00* (2006.01)
*A61F 9/06* (2006.01)
(Continued)

(52) U.S. Cl.
CPC ............ *A62B 18/006* (2013.01); *A61F 9/068* (2013.01); *A62B 7/10* (2013.01); *A62B 9/003* (2013.01);
(Continued)

(58) Field of Classification Search
CPC ..... A62B 18/006; A62B 18/02; A62B 18/025; A62B 7/10; A62B 9/003; A62B 9/006;
(Continued)

(56) References Cited

U.S. PATENT DOCUMENTS 3,045,668 A 7/1962 Lee
3,657,740 A 4/1972 Armando
(Continued)

FOREIGN PATENT DOCUMENTS

CN 2836850 11/2006
CN 102470260 5/2012
(Continued)

OTHER PUBLICATIONS

Canadian Office Action Appln. No. 3,032,951 dated Jan. 16, 2020.
(Continued)

*Primary Examiner* — Joseph D. Boecker
(74) *Attorney, Agent, or Firm* — McAndrews, Held & Malloy, Ltd.

(57) ABSTRACT

Disclosed example respirators comprise: a filter configured to filter the air; a blower fan configured to provide continuous air flow at variable speeds; an air duct configured to direct air from the blower fan to an exhaust location, the blower fan configured to blow air through the air duct; and a blower controller configured to: control the blower fan to automatically adjust an airflow speed of the blower fan to a plurality of airflow speeds over a plurality of different time periods, the plurality of airflow speeds being within an airflow speed range.

19 Claims, 7 Drawing Sheets

Related U.S. Application Data continuation of application No. 15/229,396, filed on Aug. 5, 2016, now Pat. No. 10,512,798.

(51) Int. Cl.
| | |
|---|---|
| *A62B 7/10* | (2006.01) |
| *A62B 9/00* | (2006.01) |
| *A62B 17/00* | (2006.01) |
| *F24F 11/30* | (2018.01) |
| *F24F 11/77* | (2018.01) |
| *F24F 110/10* | (2018.01) |
| *F24F 110/50* | (2018.01) |
| *A42B 3/28* | (2006.01) |

(52) U.S. Cl.
CPC .............. *A62B 9/006* (2013.01); *A62B 17/00* (2013.01); *A42B 3/286* (2013.01); *F24F 11/30* (2018.01); *F24F 11/77* (2018.01); *F24F 2110/10* (2018.01); *F24F 2110/50* (2018.01)

(58) Field of Classification Search
CPC ....... A62B 17/00; A62B 17/006; A62B 17/04; A61F 9/068; A42B 3/286
See application file for complete search history.

(56) References Cited

U.S. PATENT DOCUMENTS

| | | | |
|---|---|---|---|
| 4,293,757 A | 10/1981 | Niemi | |
| 4,815,458 A | 3/1989 | Sing | |
| 5,193,347 A * | 3/1993 | Apisdorf | G05D 23/1919 |
| | | | 62/259.3 |
| 5,318,020 A * | 6/1994 | Schegerin | A62B 18/006 |
| | | | 128/205.12 |
| 8,069,853 B2 | 12/2011 | Tilley | |
| 9,038,199 B2 | 5/2015 | Becker | |
| 9,119,979 B2 | 9/2015 | Curran | |
| 9,155,919 B2 | 10/2015 | Huh | |
| 10,512,798 B2 * | 12/2019 | Patel | A61F 9/068 |
| 11,596,815 B2 * | 3/2023 | Patel | A62B 18/006 |
| 2003/0019494 A1 * | 1/2003 | Bennett | A62B 18/006 |
| | | | 128/204.14 |
| 2004/0064171 A1 | 4/2004 | Briscoe | |
| 2005/0197684 A1 | 9/2005 | Koch | |
| 2007/0000031 A1 | 1/2007 | Makris | |
| 2007/0235030 A1 | 10/2007 | Teetzel | |
| 2008/0196723 A1 | 8/2008 | Tilley | |
| 2009/0266361 A1 | 10/2009 | Bilger | |
| 2010/0282260 A1 | 11/2010 | Sung | |
| 2011/0114093 A1 | 5/2011 | Patil | |
| 2012/0138051 A1 * | 6/2012 | Curran | A62B 7/10 |
| | | | 128/201.25 |
| 2012/0286958 A1 * | 11/2012 | Dunbar | B23K 9/322 |
| | | | 340/603 |
| 2013/0091624 A1 | 4/2013 | Czajka | |
| 2013/0139816 A1 * | 6/2013 | Proctor | A62B 18/02 |
| | | | 128/206.13 |
| 2015/0090254 A1 * | 4/2015 | Pavalarajan | A42B 3/286 |
| | | | 128/201.23 |
| 2016/0297025 A1 * | 10/2016 | Enyedy | A61F 9/068 |
| 2017/0196281 A1 * | 7/2017 | Rosati | A41D 1/002 |
| 2017/0259089 A1 | 9/2017 | De Jesus | |
| 2019/0126076 A1 * | 5/2019 | McLaughlin | H01M 10/425 |

FOREIGN PATENT DOCUMENTS

| | | |
|---|---|---|
| CN | 102665822 | 9/2012 |
| CN | 204146418 | 2/2015 |
| FR | 2867085 | 9/2005 |
| KR | 20130016256 | 2/2013 |
| KR | 101630369 | 6/2016 |
| WO | 1983000632 | 3/1983 |

OTHER PUBLICATIONS

Hans Wigö, Doctoral Thesis, Technique and human perception of intermittent air velocity variation, KTH Research School, Sep. 2005 (53 pgs.).

Int' Search Report and Written Opinion for PCT/US2017/043512 dated Oct. 11, 2017.

Office Action in Korean application No. KR 10-2019-7006460, dated Nov. 26, 2021, Korean Patent Office (8 pages).

* cited by examiner

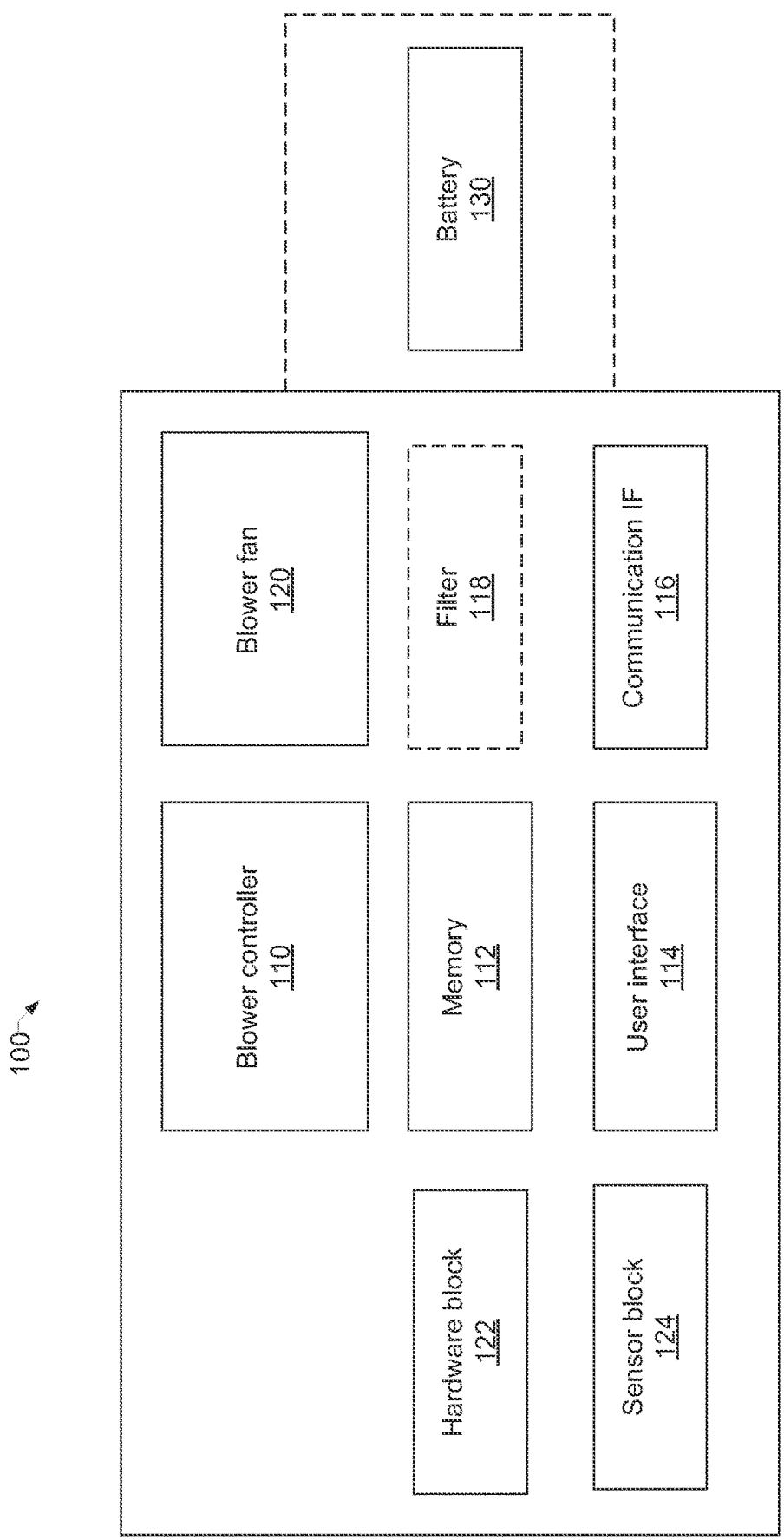

METHOD AND APPARATUS FOR PROVIDING AIR FLOW

BACKGROUND

The present disclosure relates to providing air to a user, and more particularly, to a method and apparatus for providing air flow.

Limitations and disadvantages of conventional systems for providing air to an interior of a protective device worn by a user, such as, for example, powered air purifying respirators, will become apparent to one of skill in the art, through comparison of such approaches with some aspects of the present method and system set forth in the remainder of this disclosure with reference to the drawings.

SUMMARY

Methods and systems are provided for a method and apparatus for providing air flow, substantially as illustrated by and described in connection with at least one of the figures, as set forth more completely in the claims.

BRIEF DESCRIPTION OF THE DRAWINGS

These and/or other aspects will become apparent and more readily appreciated from the following description of some example embodiments, taken in conjunction with the accompanying drawings.

FIG. 1C is a description of aa example of a blower unit in accordance with an embodiment of the disclosure.

DETAILED DESCRIPTION

Figure 1A:
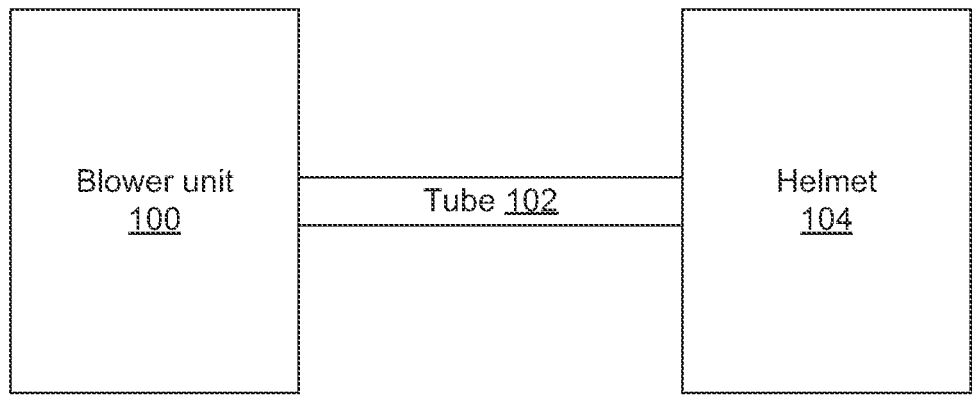
FIG. 1A is an drawing of an example of a blower unit providing air to a helmet in accordance with an embodiment of the disclosure.

Devices such as a fan for providing air can be used for various purposes, including cooling the user. However, if the user is wearing a protective device such as a helmet or protective clothing, then equipment designed for this purpose may be needed to enable the air to reach the interior of the protective device. This equipment can be generally referred to in this disclosure as a "blower unit" where the blower unit provides air to an interior of the helmet or the protective clothing to cool the user. Additionally, where the air quality is not very good because the user is in a dusty, smoky, or other undesirable environment, the air may need to be filtered before it is provided to the user, especially if the air is provided to a helmet where the air will be breathed by the user.

The filtering blower unit is also referred to as powered air purifying respirators (PAPR) or a respirator, and can be used in conjunction with, for example, welding helmets in environments where welding fumes can be hazardous or at least irritating to welders. These systems usually come with either a belt mounted or helmet mounted blower unit that blows purified air inside a positive pressure enclosure to the welder via an air duct. The blower unit consists of a fan and motor that drives air through, for example, a high efficiency particulate air (HEPA) filter to remove harmful and unwanted particles from the air stream. The filter can be before or after the fan.

A blower fan may support two or more speeds for the airflow delivered to the protective device, where the user can have an option to switch among the available speeds. A higher speed can be more desirable to the user because it provides more airflow to improve thermal comfort. However, a higher speed consumes more energy requiring more frequent replacement of batteries, or the user would use (and carry) a heavier battery pack.

An embodiment of the disclosure is a respirator configured to provide air to a protective device, where the respirator includes a filter configured to filter the air, a blower fan configured to provide continuous air flow at variable speeds, an air duct configured to direct air from the blower fan to an exhaust location, where the blower fan is configured to blow air through the air duct, and a blower controller configured to control the blower fan to adjust an airflow speed of the blower fan within an airflow speed range according to an airflow speed pattern. The respirator can include a battery as a source of power for the respirator.

The respirator comprises at least one sensor configured to detect at least one environmental condition, and the blower controller is configured to adjust the airflow speed in response to the detected environmental condition. A sensor can be a temperature sensor, where the blower controller is configured to adjust the airflow speed according to the airflow speed pattern in response to detecting that ambient temperature around the respirator has exceeded a temperature threshold and/or detecting that ambient temperature in the protective device has exceeded a temperature threshold.

A sensor can be an air quality sensor, where the blower controller is configured to adjust the airflow speed according to the airflow speed pattern in response to detecting that air quality around the respirator has fallen below a pre-determined air quality threshold and/or detecting that air quality in the protective device has fallen below a pre-determined air quality threshold.

The respirator can also comprise a communication circuit configured to receive a signal, where the blower controller is configured to use the received signal to control the blower fan to adjust the airflow speed of the blower fan. For example, the communication circuit can receive external sensor environmental information sensed by an external sensor device external to the respirator, where the blower controller is configured to adjust the airflow speed according to the airflow speed pattern in response to the received external sensor environmental information. The communication circuit can receive the environment information wirelessly or via a wired circuit.

The respirator can be set to a different minimum airflow speed including, for example, 160 liters per minute (L/min) or 170 L/min. The minimum speed may depend on where the respirator is used.

The airflow speed pattern can change the airflow speed from a first airflow speed to a second airflow speed and then change the airflow speed back to the first airflow speed, where the airflow speed pattern is completed at least once. Increasing the airflow speed can be at a first airflow change rate, and decreasing the airflow speed can be at a second airflow change rate, where the first airflow change rate and/or the second airflow change rate is a variable airflow change rate.

The respirator is configured to connect to the protective device, such as, for example, a head worn device and a protective clothing, to provide the air to an interior of the protective device. The respirator can also comprise a user interface device configured to receive input from a user, where the blower controller is configured to use the input to control the blower fan to increase the airflow speed from a lower airflow speed to a higher airflow speed for a first period of time to a first upper airflow speed.

Successive inputs received by the user interface device can also be used to increase the period of time to longer periods with each successive input until a maximum period of time is reached. Then, the next input can reduce the time period to the first period of time. Various embodiments of the disclosure can have different algorithms including, for example, reducing the time to zero to thereby bring the airflow speed back to the lower airflow speed.

Successive inputs received by the user interface device can also be used to increase the airflow speed from a lower airflow speed to higher airflow speeds with each successive input until a maximum upper airflow speed is reached. Then, the next input may reduce the airflow speed to the lower airflow speed or to the next higher airflow speed depending on the embodiment. Various embodiments may also have separate inputs for the time period and the airflow speed.

The respirator is also configured use the input to change the airflow speed pattern to another airflow speed pattern, or to use the input to control the blower fan to go from using an airflow speed pattern to output varying air flow to outputting a substantially constant air flow, or to control the blower fan to go from outputting a substantially constant air flow to using the airflow speed pattern to output varying air flow.

The blower controller is configured to control the blower fan using the airflow speed pattern by adjusting the airflow speed among a plurality of airflow speeds, where each of the plurality of airflow speeds is associated with a respective one of a plurality of time periods. Accordingly, the blower fan can blow at a lower airflow speed for a first period of time and a higher airflow speed for a second period of time, where at least one of the first period of time and the second period of time is adjustable. The number of airflow speeds and periods of times are variable depending on the implementation, and various implementations may allow adjustment of at least one of the airflow speeds and/or at least one of the periods of time.

The communication circuit is configured to receive a signal, where the blower controller uses the received signal to control the blower fan to adjust the airflow speed of the blower fan. Accordingly, there may be a remote control for the respirator.

The blower controller can be configured to control the blower fan to adjust the airflow speed of the blower fan according to the airflow speed pattern for a selected time period, and to control the blower fan to use another airflow speed pattern when the selected time period has elapsed.

Another embodiment of the disclosure is a welding helmet that includes a blower fan configured to provide continuous flow of air to an interior of the welding helmet, a blower controller configured to control the blower fan to adjust an airflow speed of the blower fan within an airflow speed range according to an airflow speed pattern, a filter to filter the air, and a battery configured to provide power to the welding helmet.

Another embodiment of the disclosure is a blower device for providing air to a protective device includes a blower fan configured to provide air flow to an interior of the protective device, a blower controller configured to control the blower fan to adjust an airflow speed of the blower fan within an airflow speed range according to an airflow speed pattern, and a battery configured to provide power to the blower device. The blower device can also include a filter to filter the air and/or at least one sensor to detect an environmental condition such as air quality, temperature, and/or humidity, where the blower controller being configured to adjust the airflow speed in response to the detected environmental condition. The protective device can be a device that is worn on the head such as, for example, a helmet, or worn on the body such as clothing or gloves/mittens.

FIG. 1A is a drawing of an example of a blower unit providing air to a helmet in accordance with an embodiment of the disclosure. Referring to FIG. 1A, there is shown a blower unit 100 that is able to provide air to an interior of the helmet 104 via the tube (or air duct) 102. Some embodiments may not include a filter for the blower unit 100. Whether a blower unit 100 has a filter can depend on the use of the blower unit 100 and the environment it is meant to be used in. For example, a blower unit 100 for welding could have a filter.

Figure 1B:
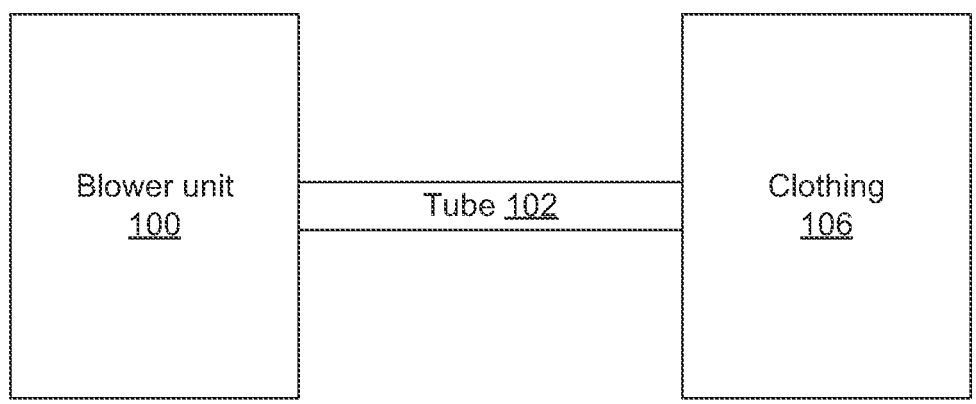
FIG. 1B is a drawing of an example of a blower unit providing air to clothing in accordance with an embodiment of the disclosure.

FIG. 1B is a drawing of an example of a blower unit providing air to clothing in accordance with an embodiment of the disclosure. Referring to FIG. 1B, there is shown a blower unit 100 that is able to provide air to the clothing 106 via the tube (or air duct) 102. Some embodiments may not include a filter for the blower unit 100. Whether a blower unit 100 has a filter can depend on the use of the blower unit 100 and the environment it is used in. For example, if the clothing 106 includes a helmet, or if the clothing 106 is used where hazardous material can damage a person due to exposure, the blower unit 100 would have a filter. Whether a blower unit 100 includes a filter is implementation dependent, and the blower unit 100 may have an option for a filter to allow the user to make a choice.

FIG. 1C is a description of an example of a blower unit in accordance with an embodiment of the disclosure. Referring to FIG. 1C, there is shown the blower unit 100 with a blower controller 110, memory 112, user interface 114, communication interface 116, filter 118, a blower fan 120, and a battery 130. The blower controller 110 can comprise hardware and/or software (also firmware) that can controller the various parts of the blower unit 100. The software can be stored in the memory 112, where the memory 112 comprises non-volatile memory, volatile memory, and/or other mass storage device. The mass storage device can be, for example, a hard drive. The memory 112 can also store other information such as, for example, airflow speed pattern, minimum and maximum airflow speeds (rates) for different uses (use in EU, USA), etc. The airflow speed pattern can comprise the airflow speed for different modes of blower unit 100 operation and the durations for the different airflow speeds.

The blower controller 110 can control the speed of the blower fan 120, receive inputs and output messages via the user interface 114, communicate with other devices via the communications interface 116, enable use of the filter 118 if such an option is available, and/or control power supplied by the battery 130.

The user interface 114 can comprise, for example, input devices such as buttons that can be pushed and/or rotated, number pads, arrow pads, keyboard, mouse, etc. The user interface 114 can also be a display (LED/LCD text/graphics/video display, LED lights, etc.) where status and/or messages can be displayed. The user interface 114 can also comprise a touch sensitive screen, and the touch sensitive screen may also be able to display text, graphics, and/or video.

The communication interface 116 can comprise hardware and/or software that can be used to exchange information with other devices via wireless or wired communication. The communication can be via protocols such as, for example, WiFi, Bluetooth, USB, etc. Some of the information that can be received by the blower unit 100 can be environmental information measured by devices external to the blower unit 100. This information can be used by the blower controller 110 to determine, for example, the airflow speed for the blower fan 120, various airflow speed patterns, etc. An airflow speed pattern can have the blower fan 120 operate at different speeds, where each speed is for a certain corresponding amount of time. For example, one airflow speed pattern can have the blower fan 120 blow at a first airflow speed for a first period of time and then for a second airflow speed for a second period of time. This cycle may then repeat continuously. The first airflow speed and the second airflow speed will be different, but the first period of time and the second period of time can be different or the same.

In some situations, the filter 118 may be needed to filter the air. The filtering can comprise removing particulates, as well as scrubbing different gases, humidity, and/or odors from the air. This can allow the user to enjoy a better air quality when the air is blown in to the user's protective device, especially if the protective device is a head worn device such as a helmet. Even when air is blown in to a non-head worn device, filtering particulates from the air can be appropriate to keep the clothes under the protective device cleaner than if the air was unfiltered.

Some embodiments might not include the filter 118 if that embodiment is to be used for cooling a user and is not expected to be in an environment with poor air quality. Other embodiments can include a filter 118 such as a HEPA filter, a carbon filter, an electrostatic filter, and/or any other types of appropriate filters. The filter 118 may be placed or removed, and the filter 118 may be replaced with a filter 118 of a different type. For example, the filter 118 can be a HEPA filter that can be replaced with a carbon filter. The blower fan 120 acts to move air, and can use any type of appropriate technology such as, for example, bladed fans or bladeless fans.

There is also a hardware logic block 122 for the general miscellaneous logic that may be present in any hardware device. The hardware logic block 122 can include, for example, timers that can be set to interrupt the blower controller 110 upon expiration of time.

The sensor block 124 can comprise one or more sensors that sense environmental conditions such as, for example, temperature, humidity, smoke, dust, etc. These environmental conditions can be used to determine the airflow speed and/or the airflow speed pattern. The environmental conditions may also be used to filter the air for those embodiments that are able to turn on and off filtering of air. These sensors in the sensor block 124 may be in the blower unit 100, on the outside of the blower unit 100, or remote sensor(s) that communicate to the blower unit 100. The blower unit 100 may also receive sensor signals from other sensors that are not part of the sensor block 124. For example, these other sensors can be part of the protective device.

The battery 130 provides power for the blower unit 100. Some embodiments can have the battery 130 separated from the rest of the blower unit 100, while other embodiments can have the battery 130 as part of the blower unit 100.

Figure 1D:
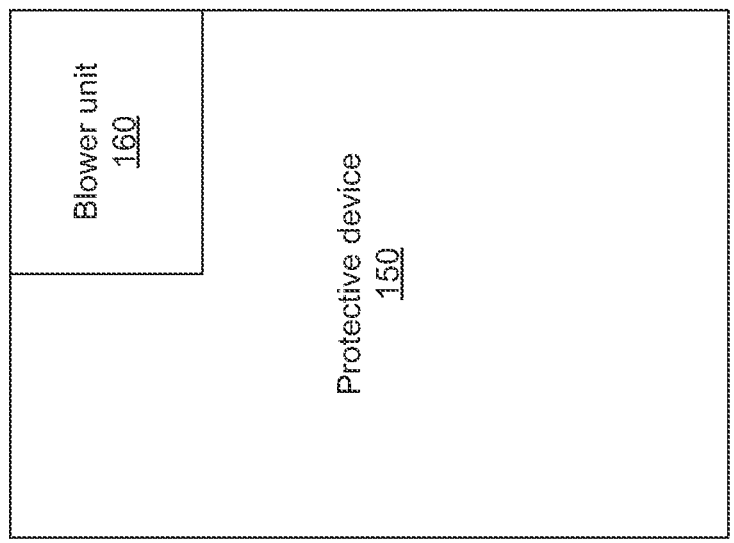
FIG. 1D is a drawing of an example of a blower unit that is a part of a protective device in accordance with an embodiment of the disclosure.

FIG. 1D is a drawing of an example of a blower unit that is a part of a protective device in accordance with an embodiment of the disclosure. Referring to FIG. 1D, there is shown a blower unit 160 that is a part of the protective device 150. If the protective device 150 is a welding helmet, the blower unit 160 would not need to be connected to the welding helmet by an air duct.

Figure 2:
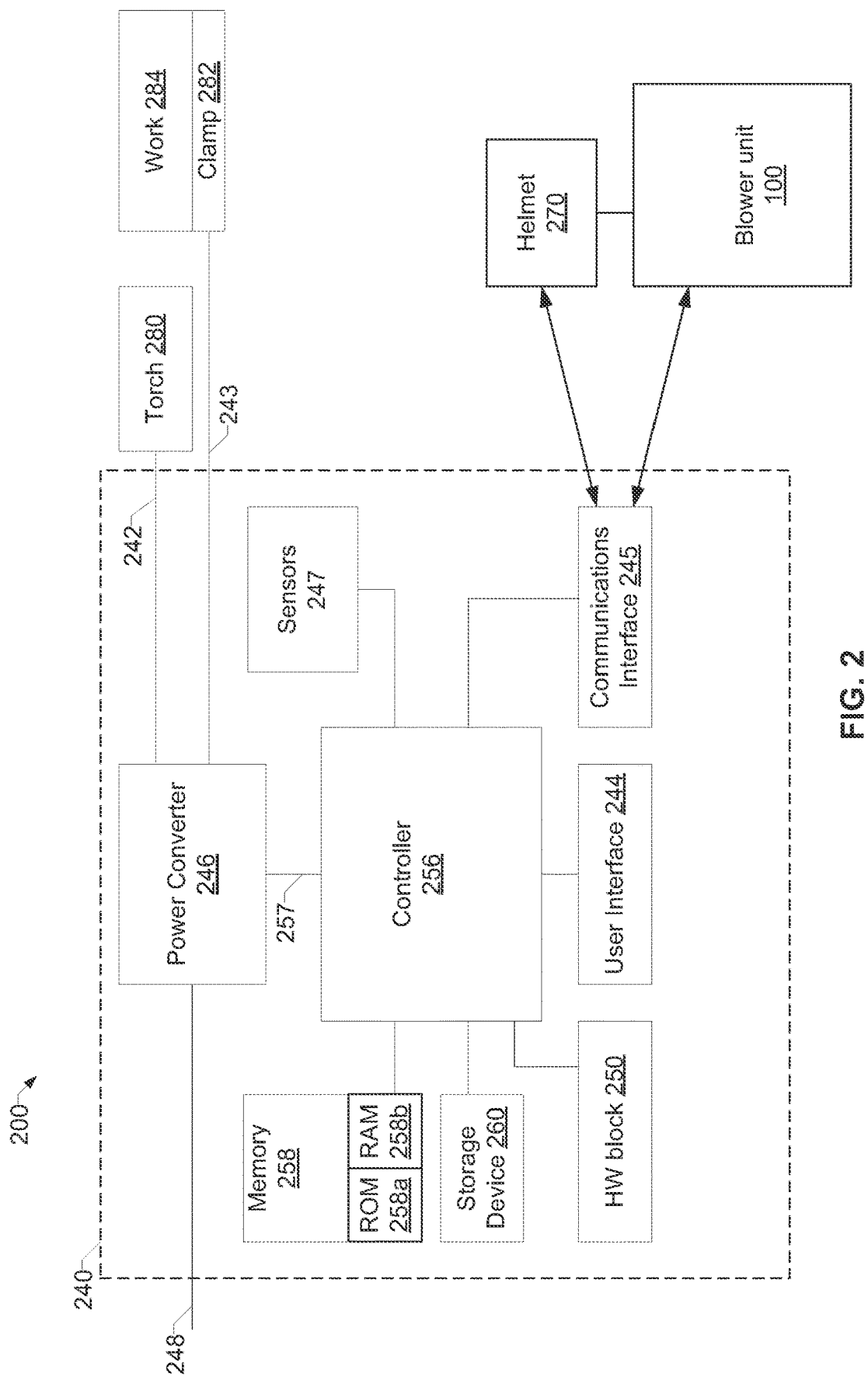
FIG. 2 is a drawing of an example of a blower unit providing air to a welding helmet in accordance with an embodiment of the disclosure.

FIG. 2 is a block diagram of an example of a blower unit providing air to a welding helmet in accordance with an embodiment of the disclosure. Referring to FIG. 2, there is shown a welding system 200 connected to the blower unit 100 providing air to an interior of the welding helmet 270 in accordance with an embodiment of the disclosure. The welding system 200 includes a power source 240 that converts input power to AC and/or DC power suitable for use in welding operations. The power source 240 includes a power converter 246 that converts input power 248 to either AC and/or DC welding power for output to a torch 280 connected to power outputs 242, 243. In the example of FIG. 2, the welding system 200 is connected to the torch 280 via the power output 242 and to the work clamp 282 via the power output 243 to form an electrical circuit with a workpiece 284 when an electrical arc is started.

The power source 240 includes a controller 256 that is operatively coupled to the power converter 246. The controller 256 may also be referred to as a welding processor. The controller 256 may be implemented using one or more of logic circuits, general-purpose microprocessors, special-purpose microprocessors, application-specific integrated circuits (ASIC), field programmable gate arrays (FPGA)s, digital signal processors (DSPs), and/or any other type of logic and/or processing device. For example, the controller 256 may include one or more digital signal processors (DSPs). Alternatively, the controller 256 could include discrete component control circuitry to perform control functions. The controller 256 controls the output power from power converter 246 by generating control signals 257 to control switching components (e.g., the SCRs) in power converter 246. The controller 256 may also generally control operation of the welding system 200.

The controller 256 receives user-selected operating parameters from the user interface 244. The controller 256 also transmits to the user interface 244 information about the welding operation that is valuable to the welder, including arc voltage, arc amperage, and/or preferred selector settings. The example user interface 244 can include any type of interface device, such as a keyboard, a pointing device (e.g., a mouse, a trackpad), a microphone, a camera (e.g., gesture-based input), a touch sensitive screen, and/or any other type of user input and/or output device.

The controller 256 can also be configured to control various aspects of the welding system 200. For example, the controller 256 can control input and output via the user interface 44 and/or the communications interface 245. As described above, the controller 256 can generically refer to a plurality of devices, including processors, which work in concert to control various aspects of the welding system 200.

In some examples, the welding system 200 can be configured to communicate via the communication interface 245 using a wired and/or wireless communication from another device. The communication can be, for example, the welding system 200 transmitting various environmental measurements sensed by the sensors 247 to the blower unit 100 and/or the welding helmet 270. The sensors 247 may be able to measure, for example, temperature, humidity, air quality, etc.

A memory device 258 and a storage device 260 are coupled to the controller 256 for storing data including the settings of the selectors on user interface 244 for future retrieval after power-down and/or between welding cycles. The memory device 258 can include a volatile memory, such as random access memory (RAM) 258b, and/or a nonvolatile memory, such as read-only memory (ROM) 258a. The storage device 260 can include magnetic media such as a hard disk, solid state storage, optical media, and/or any other short and/or long term storage device. The memory device 258 and/or the storage device 260 can store information (e.g., data) for any purpose and/or transmit stored data upon request by the controller 256. For example, the memory device 258 and/or the storage device 260 may store processor executable instructions (e.g., firmware or software) for the controller 256 to execute.

The memory device 258 can store a variety of information and can be used for various purposes. For example, the memory device 258 can store processor executable instructions (e.g., firmware or software) for the controller 256 to execute. The stored information may also comprise, for example, information regarding airflow patterns and speeds.

There is also a hardware logic block 250 for the general miscellaneous logic that may be present in any hardware device. The hardware logic block 250 may include, for example, timers that can be set to interrupt the controller 256 upon expiration of time.

The air flow speed from the blower unit 100 can be constant for a time or the air flow speed can vary depending on various conditions of the environment, and also under control of a welder. For example, the welder may control the blower unit to blow at a different constant speed, at speeds that vary over time, or at a different speed(s) for a period of time before going back to the original speed. The air flow speed can change due to environmental conditions such as temperature, humidity, air quality, etc. that can be detected by one or more sensors in the sensor block 124 in the blower unit 100 or the sensors 247 in the welding system 200. Various embodiments of the disclosure can receive the environmental condition information via, for example, the communication interface 116.

Accordingly, the cycling of air at two airflow settings creates a breathable pocket for the user above atmospheric pressure at all times and more effectively refresh the users. The blower unit 100 provides filtered air by filtering undesirable substances from welding environments at a flow rate at or above 170 L/min in the United States and at least 160 L/min in the European Union. Appropriate standards will be met by those embodiments designed for operation in other foreign countries.

When the user selects the intermittent airflow mode the fan speed controls will blow air with, for example, a lower airflow speed of 175 L/min for a period of time and a higher airflow speed of 200 L/min for another period of time at a certain frequency. Furthermore the duty cycles for the low/high airflow speeds could be symmetric or asymmetric. These variables described can be set by the manufacturer and/or customized by end users.

For reduced power consumption the rate and frequency of the oscillation can be adjusted to maximize fan efficiency to minimize power consumption. The welder has to carry the weight of the battery system and it is generally desirable to minimize this weight because it can create neck and back fatigue with prolonged use. A reduction in power consumption could be achieved by taking into account the current draw required for the motor to maintain a certain fan speed. A quicker increase in airflow speed would require a larger current draw than a more gradual increase. Thus the frequency and rate of intermittent airflow can be adjusted to take advantage of this to minimize power consumption. Similarly, as the airflow goes from its higher speed to its lower speed, the fan speed can be reduced by letting it naturally decay from the higher airflow speed to the lower airflow speed.

As stated, PAPR systems used in welding applications in the US are required to be above 170 L/min. Accordingly, a factor of safety (chosen by manufacturer or customized by end user) can also be applied and to prevent the blower unit (respirator) 100 from going below, for example, 175 L/min. Alternatively, these parameters could be automatically set through wireless communication to a sensor input such as temperature, humidity, or air quality measurement. The information obtained from these sensors could be inputted into a pre-configured algorithm that can determine the intermittent airflow parameters and/or turbo airflow mode parameters. Based on sensor inputs an algorithm could also automatically determine when to trigger and turn-off these modes.

It should be noted that these are only some examples of different sensor types and the disclosure is not limited to these particular sensor types when relating adjustable variables on the intermittent and turbo airflow modes on the PAPR system. For example, the system could also take input from the PAPR blower system to detect filter clogs or other system restrictions and modify the airflow speeds accordingly within the limits of the motor. If the "turbo" and intermittent airflow modes are not possible to be used safely within the requirements of a PAPR various embodiments of the system could provide a visual, auditory, or vibration warning to the user.

Alternate embodiments could include an input signal from a temperature sensor located externally to the blower unit or welding helmet that can wirelessly activate either an "intermittent" or "burst" mode of airflow. The input signal isn't limited to a sensor. Various controls of the blower unit 100 may be activated by a person or device remote to the blower unit 100.

With an embodiment of the disclosure, a welder can customize the pattern of intermittent air flow or burst of high velocity air flow by using, for example, the user interface 114. A user may be able to adjust parameters such as frequency of air flow variation or length of burst mode. Although various descriptions have been given for a PAPR system used with a welding helmet, the blower unit 100 can be used with any head worn protective respirator used in an industrial welding environment such as hard hats and grinding face shields, for example. The blower unit 100 can also be used with users of other protective devices such as, for example, other head worn devices and protective clothing. As described, the blower unit 100 can be integrated in a head worn protective device or other protective devices/clothing.

The blower unit 100 can also be adapted for use in a using a thermoelectric cooling device, with or without the filter 118. This can include any system where highly compressed air is released on one side of the thermoelectric device or a heat sink fin to cool the air that comes into contact with the other side those devices. The "turbo" mode for example could be linked with the release of this highly compressed air so that as air blows on to the heat sink or thermoelectric device it provides a short burst of cool air. Various embodiments can also be used with an air system that provides clean breathable air with filtered air moving through an air compressor. A digital automatic pressure regulator may be used to create the intermittent air flow.

Figure 3:
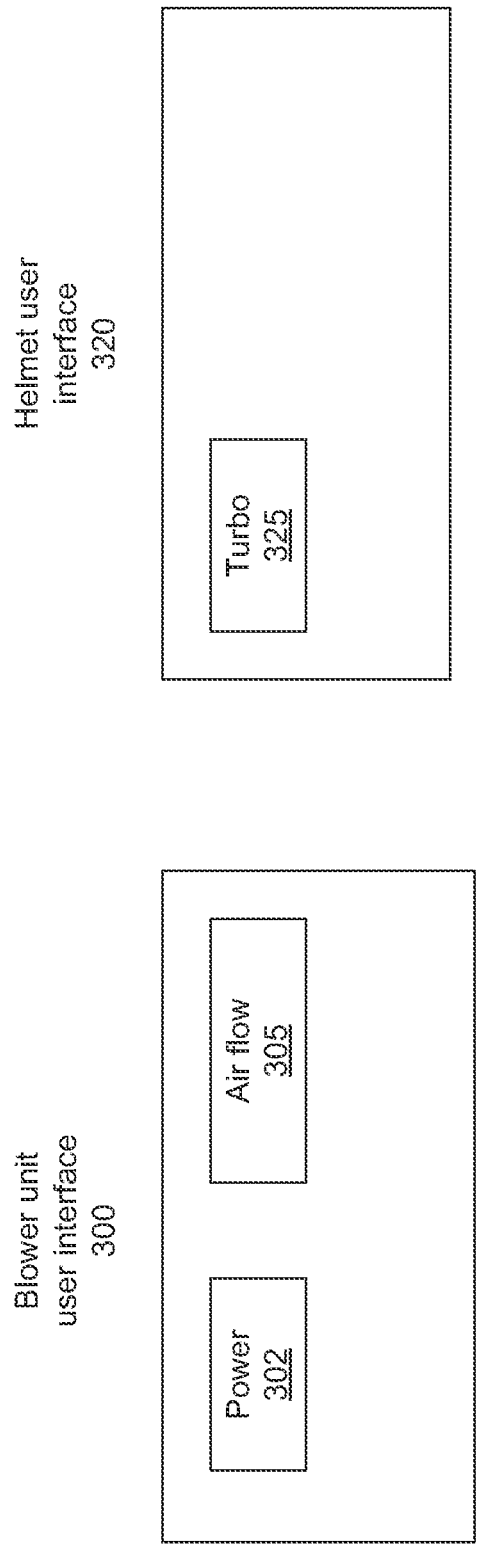
FIG. 3A is a drawing of an example of a user interface on a blower unit for controlling the blower unit in accordance with an embodiment of the disclosure.
FIG. 3B is a drawing of an example of a user interface on a helmet for controlling a blower unit in accordance with an embodiment of the disclosure.

FIG. 3A is a drawing of an example of a user interface on a blower for controlling the blower in accordance with an embodiment of the disclosure. Referring to FIG. 3A, there is shown the user interface 300 for the blower unit 100 with a power button 302 and an airflow button 305. The power button 302 can be used to turn a blower unit on and off. The airflow button 305 can be pressed, for example, to step through the different airflow modes. The airflow modes can be, for example, one or more airflow speeds, with each airflow speed on for a set period of time. There may be, for example, three different airflow modes— normal, intermittent, and turbo.

The normal mode can be a constant airflow at a certain airflow speed. The intermittent mode may cycle between two airflow speeds, with each airflow speed set for a corresponding period of time. In the intermittent mode, the airflow speed can vary from the first airflow speed to the second airflow speed then back to the first airflow speed. This can continue until the blower unit is turned off or switched to another mode. The turbo mode may be a mode where the blower unit increases the airflow speed for a certain period of time.

Various embodiments can allow changing the airflow speed(s) and/or the periods of time for the intermittent mode and/or the turbo mode. While a specific user interface was described for user input, various embodiments can use other user interfaces such as touch sensitive displays, rotary knobs, rocker switches, etc. Also, while not shown, there may be a separate button to activate the turbo mode.

FIG. 3B is a drawing of an example of a user interface on a helmet for controlling a blower unit in accordance with an embodiment of the disclosure. Referring to FIG. 3B, there is shown helmet user interface with a button 325 that controls the blower unit to enter the turbo mode as described with respect to FIG. 3A. Accordingly, the user may push or tap the button 325 for a blast of air for a period of time when he feels the need for additional air. The period of time for the turbo mode may be adjustable for various embodiments.

Various embodiments may also have more than two airflow speeds. Accordingly, each tap of, for example, the button 325 may allow the turbo mode to go to successively higher airflow speeds until a maximum airflow speed is reached. The next tap of the button 325 may then bring the airflow speed to the lowest airflow speed. Another embodiment of the disclosure may bring the airflow speed from the maximum airflow speed to the first airflow speed above the lowest airflow speed.

Additionally, each tap of, for example, the button 325 may allow the turbo mode to go to successively to longer periods of time until a maximum period of time is reached. The next tap of the button 325 may then bring the period of time to the first (smallest) period of time. Various embodiments of the disclosure can have different algorithms including, for example, reducing the time from maximum to zero to thereby end the turbo mode to bring the airflow speed back to the lowest airflow speed.

Still other embodiments may allow changing the airflow speeds and the periods of time.

Figure 4:
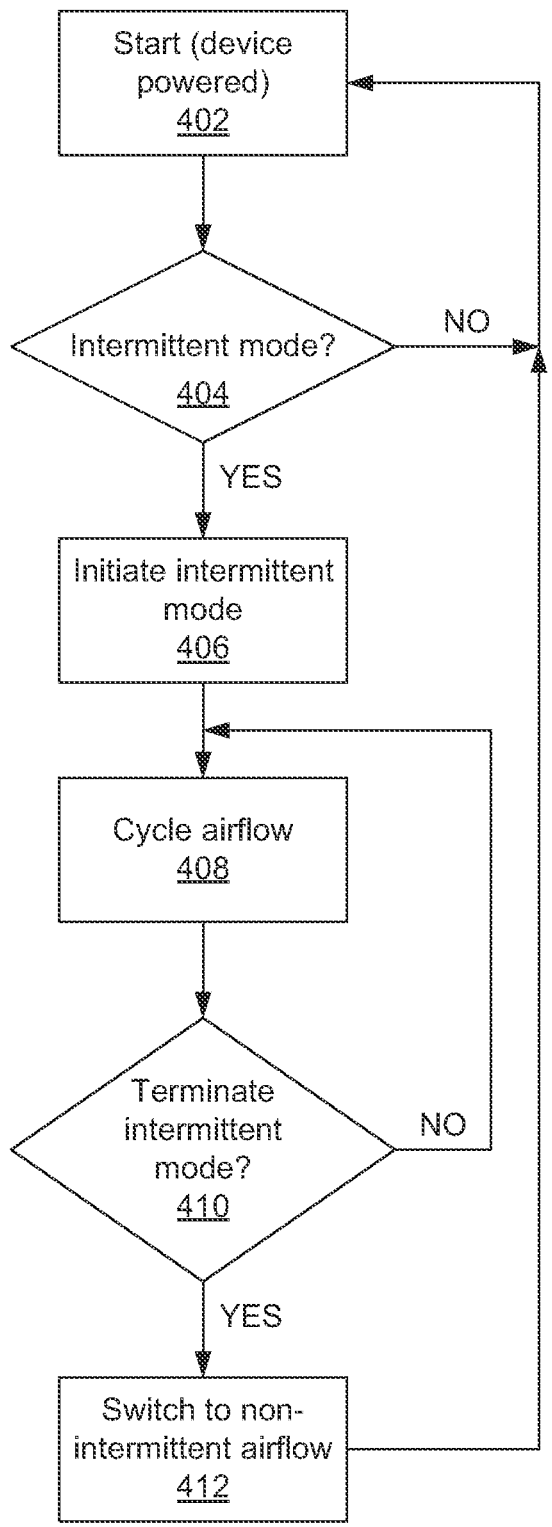
FIG. 4 is an example of a flow chart for a blower unit in accordance with an embodiment of the disclosure.

FIG. 4 is an example of a flow chart for a blower unit in accordance with an embodiment of the disclosure. Referring to FIG. 4, references to devices described in the previous figures will be made for convenience of description. At 402, the blower unit 100 may be powered on and in a state of providing continuous airflow at a constant first airflow speed. Depending on the usage of the blower unit 100, the airflow may be continuous at a minimum airflow speed to meet regulatory requirements. For example, presently, in the United States a respirator should have a minimum airflow speed of 170 L/min and 160 L/min in the European Union. At 404, the blower controller 110 may check to see if an intermittent mode may be requested. If not, the blower unit 100 may stay at the constant first airflow speed. If intermittent mode has been requested, the blower unit 100 initiates intermittent mode at 406 using the first airflow speed and a second airflow speed according to the airflow speed pattern that is in use.

At 408, the blower unit 100 will control the blower fan 120 to an appropriate second airflow speed. It should be noted that at 408, the blower controller 110 switches the blower fan 120 to operate at the second airflow speed if it is presently operating at the first airflow speed, and vice versa. After the blower fan has been operating for the second airflow speed for a corresponding period of time indicated in the airflow speed pattern, the blower controller 110 checks at 410 whether to exit the intermittent mode. If so, the blower controller 110 sets the blower fan 120 to blow at the constant first airflow speed at 412 and the blower unit 100 returns to 402.

If the blower unit 100 is to remain in the intermittent mode, the other airflow speed is set for the blower fan 120 at 408, and the flow chart operations continue.

While FIG. 4 shows explicit stages for an example flowchart, other embodiments can use different stages or different methodology. For example, the flowchart of FIG. 4 may be performed with software instructions, or the control may also be done using a hardware state machine in the hardware logic block 122 or 250, or some combination of hardware state machine and software control may be used. A timer may also be used for some functionality such as, for example, waiting for the appropriate time periods before switching from the first airflow speed to the second airflow speed, and from the second airflow speed to the first airflow speed. The expiration of time may be indicated by a number of different methods. For example, expiration of time may trigger an interrupt, a flag may be set, a hardware signal may be set, etc.

Additionally, while two different airflow speeds were given as examples, various embodiments need not be so limited. The number of airflow speeds and the switching from one airflow speed to another are implementation dependent.

Figure 5:
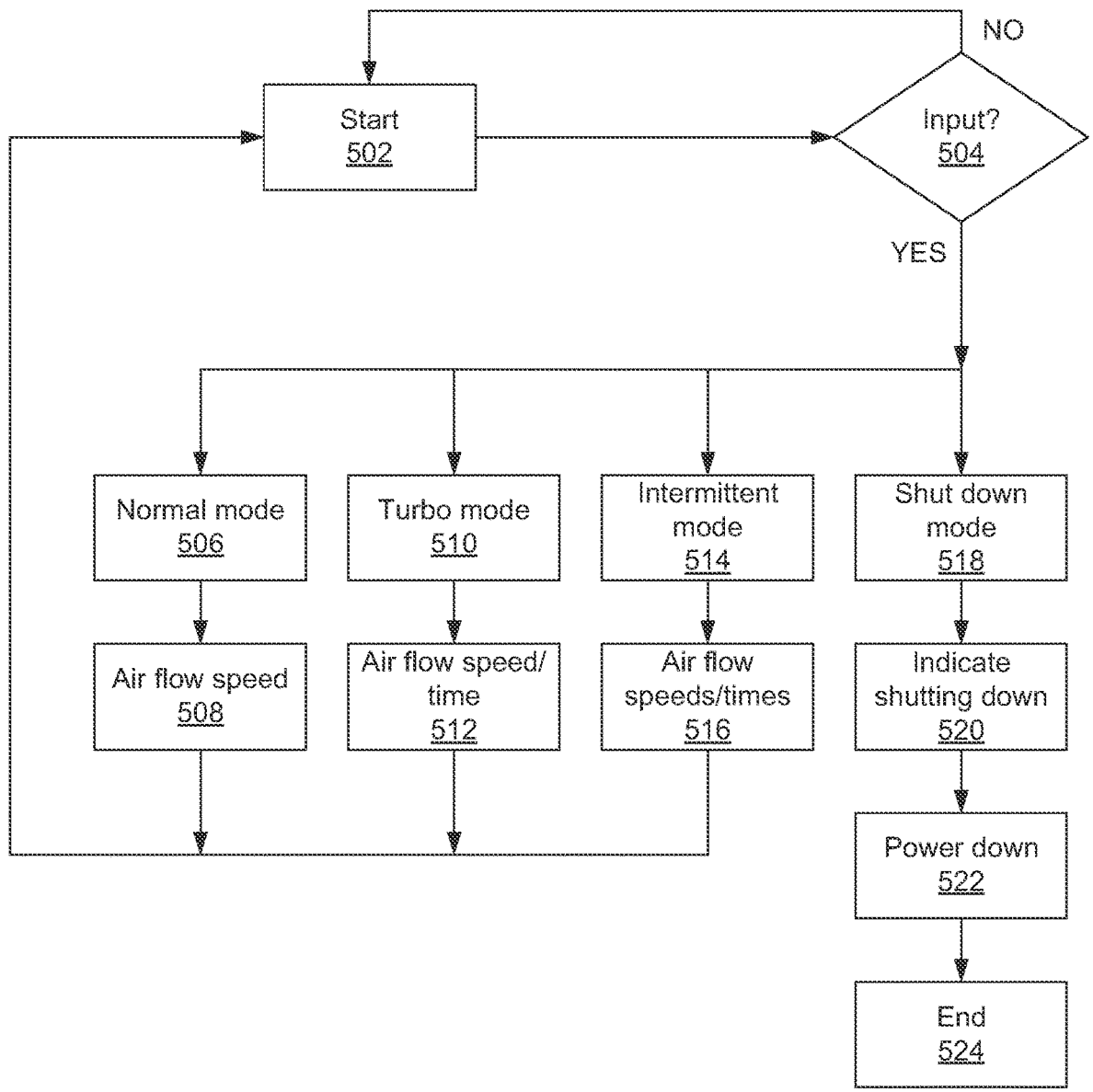
FIG. 5 is an example of a flow chart for a blower unit in accordance with an embodiment of the disclosure.

FIG. 5 is an example of a flow chart for a blower unit in accordance with an embodiment of the disclosure. Referring to FIG. 5, references to devices described in the previous figures will be made for convenience of description. The blower unit 100 may be in a run state at 502, where the blower unit 100 is running in a selected mode. The blower unit 100 may start, for example, when the power button 302 is pressed and may run at 502. The blower unit 100 may start in a default state of constant first airflow speed, for example. Other embodiments may start in the last mode that the blower unit 100 was in when it was turned off. Other embodiments may start in the turbo mode. The mode in which the blower unit 100 starts may be set to different options for different embodiments. Various embodiments may also allow the start mode to be selected by a user as part of a setup option.

Additionally, depending on the usage of the blower unit 100, the airflow may be continuous at a minimum airflow speed to meet regulatory requirements. For example, presently, in the United States a respirator should have a minimum airflow speed of 170 L/min and 160 L/min in the European Union.

At 504, the blower controller 110 checks to see if there is any input for the blower fan mode. For example, in an embodiment, a user can enter via the user interface 300 and/or 320 whether to use a normal (constant airflow speed) mode, an intermittent airflow speed mode, or a turbo mode, and also to turn off the blower unit 100.

If the input indicates a normal mode, then at 506 the blower controller 110 sets the blower fan 120 for normal mode. At 508, the blower controller 110 controls the blower fan 120 to blow at the constant first airflow speed. Then the blower unit 100 may start the process again by running at the selected speed at 502. The first airflow speed may be adjustable in various embodiments of the disclosure.

If the input indicates a turbo mode, then at 510 the blower controller 110 sets the blower fan 120 for turbo mode. At 512, the blower controller 110 controls the blower fan 120 to blow at the second airflow speed for a period of time where the second airflow speed is greater than the first airflow speed. Then the blower unit 100 may start the process again by running the blower fan at the second airflow speed at 502 for the period of time. After the period of time is up, the blower fan 120 at the first airflow speed.

If the input indicates intermittent mode, then at 514 the blower controller 110 sets the blower fan 120 for intermittent mode. At 516, the blower controller 110 controls the blower fan 120 to blow at the first airflow speed for a first period of time, and at a second airflow speed for a second period of time, where the second airflow speed is greater than the first airflow speed. Then the blower unit 100 may start the process again by running at the appropriate speed at 502. Accordingly, the blower fan 120 will blow air at the two different speeds until the blower unit 100 exits the intermittent mode.

The first period of time may be independent of the second period of time. The airflow speeds and the periods of time for the various modes are dependent on the airflow speed pattern. The airflow speed pattern may be adjustable in various embodiments of the disclosure.

The periods of time for the first airflow speed and/or the second airflow speed may be measured using any appropriate technology that may be appropriate. For example, the time may be measured by software loops, or a timer in the hardware logic block 122 or 250 may be set and the timer may be checked periodically or the timer may set an interrupt upon reaching the time it is set to count. A timer may also be available, for example, in the blower controller 110 or another processor such as the controller 256.

If the input indicates that the blower unit 100 should be shut off, the blower unit 100 will enter shutdown mode at 518. The shutdown mode 518 may include, for example, saving the present mode into memory 112 to use the next time the blower unit 100 is turned on. At 520, an indication of shutdown may be output to the user interface 114 and/or 244. The indication may be flashing an LED, turning on an LED, or displaying a message indicating shutdown, or some other appropriate indication. The power may be turned off at 522, and the flowchart is at an end stage at 524.

Various embodiments disclose changing the airflow speed from a lower speed to a higher speed and vice versa. During the changing of the speed, the rate of change of speed may be different when going from high speed to low speed and when going from low speed to high speed. For example, when going from high speed to low speed, power to the blower fan 120 can be reduced or removed to let the blower fan 120 slow down by itself. Going from low speed to high speed may use different amounts of power depending on the remaining capacity of the battery 130 and/or other parameters that may be used by the blower controller 110. However, the blower fan 120 may also use power to slow down the blower fan 120 more quickly. Again, the amount of power used may be controlled by the blower controller 110. Accordingly, the rate of change for changing the airflow speed can be variable.

Again, while an example flow diagram has been described, various embodiments need not be limited to this example. For example, the number of airflow speeds and the switching from one airflow speed to another are implementation dependent.

The present methods and systems may be realized in hardware, software, and/or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may include a general-purpose computing system with a program or other code that, when being loaded and executed, controls the computing system such that it carries out the methods described herein. Another typical implementation may comprise one or more application specific integrated circuit or chip. Some implementations may comprise a non-transitory machine-readable (e.g., computer readable) medium (e.g., FLASH memory, optical disk, magnetic storage disk, or the like) having stored thereon one or more lines of code executable by a machine, thereby causing the machine to perform processes as described herein. As used herein, the term "non-transitory machine-readable medium" is defined to include all types of machine readable storage media and to exclude propagating signals.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x,y)}. In other words, "x and/or y" means "one or both of x and y". As another example, "x, y, and/or z" means any element of the seven-element set {(x), (y), (z), (x,y), (x,z), (y,z), (x,y,z)}. In other words, "x, y and/or z" means "one or more of x, y and z". As utilized herein, the term "exemplary" means serving as a non-limiting example, instance, or illustration. As utilized herein, the terms "e.g." and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

The present methods and/or systems may be realized in hardware, software, or a combination of hardware and software. The present methods and/or systems may be realized in a centralized fashion in at least one computing system or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, the present method and/or system are not limited to the particular implementations disclosed. Instead, the present method and/or system will include all implementations falling within the scope of the appended claims, both literally and under the doctrine of equivalents.

What is claimed:

1. A respirator configured to provide air to a protective device, comprising:
   a filter configured to filter the air;
   a blower fan configured to provide continuous air flow at variable speeds;
   an air duct configured to direct air from the blower fan to an exhaust location, the blower fan configured to blow air through the air duct;
   a blower controller configured to:
      control the blower fan to automatically adjust an airflow speed of the blower fan to a plurality of airflow speeds over a plurality of different time periods, the plurality of airflow speeds being within an airflow speed range, by changing from a first airflow speed of the plurality of airflow speeds to a second airflow speed of the plurality of airflow speeds at a variable airflow change rate.

2. The respirator as defined in claim 1, further comprising at least one sensor configured to detect at least one environmental condition, the blower controller being configured to adjust the airflow speed in response to the detected environmental condition.

3. The respirator as defined in claim 2, wherein the at least one sensor is a temperature sensor, the blower controller being configured to adjust the airflow speed according to an airflow speed pattern in response to detecting that ambient temperature around the respirator has exceeded a temperature threshold.

4. The respirator as defined in claim 2, wherein the at least one sensor is an air quality sensor, the blower controller being configured to adjust the airflow speed according to an airflow speed pattern in response to detecting that air quality around the respirator has fallen below a pre-determined air quality threshold.

5. The respirator as defined in claim 2, further comprising a communication circuit configured to receive external sensor environmental information sensed by an external sensor device external to the respirator, wherein the blower controller is configured to adjust the airflow speed according to an airflow speed pattern in response to the received external sensor environmental information.

6. The respirator as defined in claim 5, wherein the communication circuit receives the external sensor environmental information wirelessly.

7. The respirator as defined in claim 2, wherein the at least one sensor is a temperature sensor, the blower controller being configured to adjust the airflow speed according to an airflow speed pattern in response to detecting that ambient temperature in the protective device has exceeded a temperature threshold.

8. The respirator as defined in claim 2, wherein the at least one sensor is an air quality sensor, the blower controller being configured to adjust the airflow speed according to an airflow speed pattern in response to detecting that air quality in the protective device has fallen below a pre-determined air quality threshold.

9. The respirator as defined in claim 1, wherein the airflow speed range includes a lower airflow speed of at least 160 liters per minute.

10. The respirator as defined in claim 1, wherein the airflow speed range includes a lower airflow speed of at least 170 liters per minute.

11. The respirator as defined in claim 1, further comprising a battery configured to provide power to the respirator.

12. The respirator as defined in claim 1, further comprising the protective device coupled to the exhaust location of the air duct.

13. The respirator as defined in claim 12, wherein the respirator is configured to connect to the protective device to provide the air to an interior of the protective device.

14. The respirator as defined in claim 12, wherein the protective device is one of: a head worn device and a protective clothing.

15. The respirator as defined in claim 1, further comprising a user interface device configured to receive an input from a user, wherein the blower controller is configured to use the input to control the blower fan to increase the airflow speed for a first period of time to a first upper airflow speed.

16. The respirator as defined in claim 15, wherein the blower controller is configured to increase the first period of time to a longer period with each successive input received by the user interface device until a maximum period of time is reached, wherein a next input received by the user interface device decreases the maximum period of time to the first period of time.

17. The respirator as defined in claim 15, wherein the blower controller is configured to increase the first upper airflow speed to a higher upper airflow speed with each successive input received by the user interface device until a maximum upper airflow speed is reached, wherein a next input received by the user interface device decreases the maximum upper airflow speed to the first upper airflow speed.

18. The respirator as defined in claim 1, further comprising a user interface device configured to receive an input from a user, wherein the blower controller is configured to use the input: to control the blower fan to toggle between outputting varying air flow and outputting a substantially constant air flow.

19. A respirator configured to provide air to a protective device, comprising:
  a filter configured to filter the air;
  a blower fan configured to provide continuous air flow at variable speeds;
  an air duct configured to direct air from the blower fan to an exhaust location, the blower fan configured to blow air through the air duct;
  a user interface device configured to receive an input from a user, wherein the blower controller is configured to use the input to control the blower fan to increase the airflow speed for a first period of time to a first upper airflow speed; and
  a blower controller configured to:
    control the blower fan to automatically adjust an airflow speed of the blower fan to a plurality of airflow speeds over a plurality of different time periods, the plurality of airflow speeds being within an airflow speed range; wherein the blower controller is configured to increase the first period of time to a longer period with each successive input received by the user interface device until a maximum period of time is reached, wherein a next input received by the user interface device decreases the maximum period of time to the first period of time.

* * * * *